United States Patent
Kume et al.

(10) Patent No.: US 7,427,407 B2
(45) Date of Patent: Sep. 23, 2008

(54) COSMETICS

(75) Inventors: Takuji Kume, Tokyo (JP); Hiromitsu Kawada, Tokyo (JP); Yasuhiro Jisai, Tokyo (JP); Tomohiko Sano, Tokyo (JP)

(73) Assignee: Kao Corporation, Tokyo (JP)

( * ) Notice: Subject to any disclaimer, the term of this patent is extended or adjusted under 35 U.S.C. 154(b) by 759 days.

(21) Appl. No.: 10/468,393

(22) PCT Filed: Feb. 28, 2002

(86) PCT No.: PCT/JP02/01852

§ 371 (c)(1),
(2), (4) Date: Aug. 28, 2003

(87) PCT Pub. No.: WO02/067874

PCT Pub. Date: Sep. 6, 2002

(65) Prior Publication Data

US 2004/0071747 A1   Apr. 15, 2004

(30) Foreign Application Priority Data

Feb. 28, 2001 (JP) .............................. 2001-053843
Jun. 19, 2001 (JP) .............................. 2001-184475

(51) Int. Cl.
*A61K 8/00*   (2006.01)
*A61K 31/74*  (2006.01)
*A61K 8/02*   (2006.01)

(52) U.S. Cl. ..................... 424/401; 424/78.08; 424/400

(58) Field of Classification Search .................. 424/401, 424/78.08, 400
See application file for complete search history.

(56) References Cited

U.S. PATENT DOCUMENTS 6,143,310 A * 11/2000 Sang et al. .................. 424/401

FOREIGN PATENT DOCUMENTS

| JP | 57-112314  | 7/1982  |
|----|------------|---------|
| JP | 2-36114    | 2/1990  |
| JP | 3-284610   | 12/1991 |
| JP | 9-95422    | 4/1997  |
| JP | 9-263528   | 10/1997 |
| JP | 10-298030  | 11/1998 |
| JP | 11-269032  | 10/1999 |
| JP | 2000-119162 | 4/2000 |
| JP | 2000-302639 | 10/2000 |
| JP | 2001-72566 | 3/2001  |

* cited by examiner

*Primary Examiner*—Shelley A. Dodson
(74) *Attorney, Agent, or Firm*—Oblon, Spivak, McClelland, Maier & Neustadt, P.C.

(57) ABSTRACT

Cosmetics containing the following components (A) and (B): (A) an oil-absorbing powder having a squalane-absorbing ability of 1 ml/g or more; and (B) a compound having an affinity for component (A) lower than that of sebum, and having an ability to absorb the sebum and release component (B) in exchange for the sebum when the cosmetic is applied onto the skin. These cosmetics can adequately absorb the sebum and thus exhibit excellent effects of relieving or preventing oiliness of the skin and worsening in makeup. By selecting an appropriate compound to be released in exchange for the absorbed sebum, a substance capable of improving the skin qualities such as moistness, tightness, and tension can be allowed to penetrate into the skin. Moreover, a bodily feeling of the removal of the sebum can be imparted to users thereby.

9 Claims, No Drawings

COSMETICS

TECHNICAL FIELD

The present invention relates to cosmetics used for applying or adhering onto the skin such as face for sebum absorption.

BACKGROUND

On the surface of epidermis, a thin sebaceous film is formed. Such film has actions for preventing foreign matters in the environment from entering into the epidermis, for protecting the skin from irritation of various substances, or minimizing moisture loss for humectating the skin surface. On the other hand, an excess sebum causes an oily feeling in touch, greasy and shiny skin and worsening in makeup, and also causes seborrheic dermatitis such as acne.

Therefore, several methods such as those for physiologically suppressing the sebaceous secretion using pharmacologically active substances and physically absorbing an excessively secreted sebum with an oil-adsorbing substance have been examined. However, any useful pharmacologically active substance effective for sebum suppression has not been discovered, and is not in practical use.

A method for removing an excess sebum in the latter using a grease-absorbing paper is known, but this method is not satisfactory in a sebum-absorbing ability, though acceptable as a first-aid treatment. Further, for example, a pack containing lipophilic titanium dioxide or lipophilic silicon dioxide (JP-A-57-112314); a cosmetic containing healstone (Bakuhanseki) powder with a median particle diameter of 5-15 μm (JP-A-09-263528); and a cosmetic sheet containing porous granules (microcapsules) encapsulating a functional treating agent attached onto the surface or inside of a sheet material (JP-A-02-36114) have been proposed, but these are not satisfactory for practical use and in sebum-absorbing ability, and further are deficient in an actual feeling of the removal of the sebum as compared with the grease-absorbing paper. In order to improve an actual feeling of sebum-free, for example, in the grease-absorbing paper, a method is known in which a pattern on the paper disappears or becomes clear when sebum is absorbed (JP-A-10-298030), but the method can not be broadly applied for various types of cosmetics.

In JP-A-2001-72566, a sheet-like pack cosmetic comprising an oil-absorbing powder, which absorbs a specific amount of squalane, is described. This pack cosmetic is superior in sebum-absorbing ability as well as in improving and preventing worsening in makeup; however, in order to supplement effects such as moistness, tightness and tension, additional cosmetics such as lotion and cream have to be used.

An object of the present invention is to provide a cosmetic which can adequately absorb sebum and thus exhibit a superior effect of improving or preventing oiliness of the skin and worsening in makeup, is easy to use, imparts an actual feeling of the removal of the sebum to users, as well as effectively provides a substance having an ability to improve the skin qualities such as moistness, tightness and tension to the skin.

DISCLOSURE OF THE INVENTION

The present inventors have found that combined use of an oil-absorbing powder having a specific squalane-absorbing ability (squalane-absorptivity) and a compound having an affinity for said oil-absorbing powder lower than that of sebum can adequately absorb the sebum, thus leading to exhibiting a superior effect in improving or preventing oiliness of the skin and worsening in makeup. Further, the present inventors have found that, by suitably selecting a compound having an affinity for the oil-absorbing powder lower than the affinity of sebum, a component which improves the skin qualities such as moistness, tightness and tension can be released from the cosmetic in exchange for the absorbed sebum, and thus allowed to penetrate effectively into the skin, and also found that such cosmetics can be obtained which are superior in the effect of imparting a bodily feeling of the safe removal of the sebum to users.

The present invention provides a cosmetic comprising the following components (A) and (B):

(A) an oil-absorbing powder having a squalane-absorbing ability of 1 ml/g or more;
(B) a compound having an affinity for component (A) lower than that of sebum, and having an ability to absorb the sebum and release component (B) in exchange for the sebum when the cosmetic is applied onto the skin.

BEST MODE FOR CARRYING OUT THE INVENTION

The cosmetic of the present invention can be produced by mixing component (A) and component (B) or an aqueous medium dissolving component (B), and homogeneously dispersing the components. A state of "homogeneously dispersed" means a state in which the surface of the powder of component (A) is sufficiently wetted with component (B) or an aqueous medium dissolving component (B), and component (B) or the aqueous medium dissolving component (B) is incorporated into the spaces among the particles of the powder. Further, the phrase "absorb sebum and then release component (B) in exchange for the sebum when applied to the skin" means that, since component (A) has an affinity for sebum, i.e. an oil, higher than that of component (B) or an aqueous medium dissolving component (B), and is easily wetted with sebum, when the cosmetic of the present invention comes into contact with the sebum, the sebum is surrounded by the periphery of component (A), and as a result, component (B), which has an affinity lower than that of sebum, is released in exchange for the sebum.

The oil-absorbing powder of component (A) used in the present invention has a squalane-absorptivity of 1 ml/g or more, preferably 1.5 ml/g or more to absorb sebum sufficiently.

The squalane-absorptivity used herein is a value as measured according to the method for measurement of oil-absorptivity of dyestuffs defined in JIS K5101 (1978). Namely, 1 g of powder is weighed on a glass plate, and added dropwise with squalane thereon while kneading with spatula to prepare a paste. An end point of addition is set at the time when the powder takes totally a paste form, and the amount of squalane (ml) at the end point is defined as a value of oil-absorptivity (ml/g).

Examples of the oil-absorbing powder include vinyl polymers obtained by polymerizing one or more monomers such as vinyl acetate, N-vinylpyrrolidone, methacrylates, acrylates, styrene and divinylbenzene; nylon; and silicic anhydride. These powders are preferably porous, and a squalane-absorptivity can be adjusted by a conventional method.

Among them, a lipophilic oil-absorbing powder of vinyl polymers, nylon or the like is preferable since the oil-absorptivity thereof is not decreased by water or sweat.

The above-mentioned vinyl polymer is preferably a porous lipophilic polymer obtained by polymerizing one or more vinyl monomers having a solubility parameter of 7-10. The vinyl monomer having a solubility parameter of 7-10 includes, for example, (meth)acrylic acid; diolefins having 4 to 6 carbon atoms; styrene or styrene derivatives having a hydrocarbon substituent having 1 to 12 carbon atoms; esters of (meth)acrylic acid and higher alcohols having 8 to 24 carbon atoms; and esters such as vinyl esters of saturated carboxylic acids having 8 to 20 carbon atoms. Superior compatibility with sebum and a high sebum-absorptivity can be obtained by the monomers having a solubility parameter of 7-10.

In the present invention, preferably the oil-absorbing powder is swollen with sebum, but not be soluble in sebum from the viewpoint of feeling, and thus is preferably cross-linked. Cross-linking can be performed by adding polyfunctional monomer in a polymerization process, by post-crosslinking, or by self-crosslinking. The polyfunctional monomers include, for example, divinylbenzene, divinylpyridine, ethylene glycol di(meth)acrylate and triethyleneglycol di(meth)acrylate.

Polymerization of the above-mentioned vinyl monomers and formation of a porous structure are preferably performed, for example, by a method described in JP-A-63-316715, namely, a method comprising dissolving a monomer in a non-polymerizable organic solvent, polymerizing the solution in a state suspended, dispersed or emulsified in water, and removing said organic solvent after termination of the polymerization.

Commercially available examples of such oil-absorbing powder include porous nylon powders such as Orgasol 2002 (Elf Autochem. Corp.); a cross-linked elastomer of dimethyl silicone such as Torayfil E-506C (Dow Corning Toray Silicone Co. Ltd.); polymethyl methacrylates such as Microsphere M-100, Microsphere M-300, Microsphere M-400 and Microsphere R-109 (Matsumoto Yushi Co. Ltd.); and methacrylate copolymers such as Polytrap (Dow Corning Inc.).

The oil-absorbing powder used in the present invention has a mean particle diameter of 0.005-30 µm, preferably 0.005-20 µm, as measured by a laser diffraction/scattering method. Further, in the oil-absorbing powder, particles having a particle diameter in a range of 0.005-30µm amount to preferably 90% by weight or more.

A mixture of two or more of the oil-absorbing powders may be used, and is contained in 10-60% by weight, preferably in 30-60% by weight of the whole composition. A cosmetic containing the oil-absorbing powder within these ranges is preferable because the oil-absorbing powder forms a sequential chain structure in the cosmetic and can absorb sebum effectively, and further homogeneous kneading is facilitated in the production of the cosmetic.

In addition, the above-mentioned hydrophobic oil-absorbing powder is preferably contained in an amount of 5% by weight or more, preferably 10-40% by weight, of the whole composition.

The compound of component (B) used in the present invention essentially should have an affinity for the oil-absorbing powder lower than that of sebum, in order to be released in exchange for the sebum when the oil-absorbing powder absorbs the sebum. Preferably, the compound has a solubility in water higher than a solubility in squalane.

Component (B) includes active ingredients such as humectants, pharmacologically active substances, antibiotics and antiinflammatory agents; and water-soluble dyestuffs.

The active ingredients include extracts of animals or plants, amino acids or salts thereof, peptides, proteins, organic acids, vitamins and derivatives thereof, urea and inorganic salts. More specifically, the active ingredients include the following substances.

Extracts of animals and plants: Extracts of animals include placenta extract, and water-soluble placenta extract, which is commercially available and used as a raw material of cosmetics, can be used. For example, products obtained from placenta of mammals such as bovine, swine or human through processings such as washing, removal of brood, mincing and freeze drying, followed by extracting water-soluble components, and further removing impurities, are included. Plant extracts include, for example, extracts obtained from the following plants: *Angelica keiskei*, *Vigna angularis* (adzuki bean), Catechu, *Persea americana* (avocado), *Hydrangea macrophylla*, *Gynostemma pentaphyllum*, *Althaea officinalis* (marshmallow), Altoca, *Arnica montana*, *Prunus dulcis* (almond), *Aloe arborescens* (candelabra aloe), *Prunus armeniaca* (apricot), Uritica, Iris, *Foeniculum vulgare* (fennel), *Curcuma longa* (turmeric), *Rosa multiflora* (rose fruit), *Scutellaria baicalensis* (scutellaria root), *Phellodendron amurense* (phellodendron bark), *Coptis japonica* (coptis rhizome), *Hordeum vulgare* (barley), *Abelmoschus esculentus* (okra), *Hypericum erectum*, Lamium, Ononis, *Nasturtium officinale* (watercress), *Diospyros kaki*, *Pueraria lobata* (pueraria root), *Valeriana fauriei* (Japanese valerian), Betula (birch), Typha (cattail), *Matricaria chamomilla* (chamomile), Avena (oats), *Glycyrrhiza globra* (glycyrrhiza), Rubus (bramble, raspberry), *Actinidia chinensis* (kiwi berry), *Cinchona succirubra* (cinchona bark), *Cucumis sativus* (cucumber), Japanese apricot seed, *Aleurites moluccana* (candlenut tree), *Gardenia jasminoides* (gardenia), *Sasa veitchii* (kuma bamboo grass), *Juglans regia* (English walnut), *Cinnamomum cassia* (cinnamon bark), *Morus alba* (white mulberry), Gunjo, *Gentiana lutea* (gentian), *Geranium thunbergii* (geranium herb), *Magnolia obovata* (magnolia bark), *Panax ginseng* (ginseng), *Arctium lappa* (edible burdock), *Sesamum indicum* (sesame), *Triticum aestivum* (wheat), *Symphytum officinale* (comfrey), *Oryza sativa* (rice), *Camellia sasanqua* (sasanqua), *Crocus sativus* (saffron), *Crataegus cuneata* (crataegus), *Zanthoxylum piperitum* (Japanese pepper), *Lentinus edodes* (shiitake), *Rehmannia glutinosa* (rehmannia root), *Lithospermum erythrorhizon* (lithospermum root), *Perilla frutescens* (perilla seed), Tilia (lime), Filipendula (meadowsweet), *Paeonia lactiflora* (peony root), *Zingiber officinale* root (ginger), *Zingiber officinale* (ginger), *Acorus calamus* root, *Betula platyphylla* var. *japonica* (Japanese white birch), *Lonicera japonica* (gold-and-silver flower), *Equisetum arvense* (common horsetail), *Stevia rebaudiana* (stevia), *Hedera helix* (English ivy), *Crataegus laevigata* (white thorn), *Sambucus nigra* (European elder), *Juniperus communis* (common juniper), *Achillea millefolium* (milfoil), *Mentha piperita* (peppermint), *Salvia officinalis* (common salvia), *Malva sylvestris* (cheeses), *Cnidium officinale* root (cnidium rhizome), savory, *Morus bombycis* bark (mulberry bark), *Glycine max* seed (soybean), *Zizyphus jujube* fruit (jujube fruit), *Thymus vulgaris* (thyme), *Thea sinensis* (tea), *Syzygium aromaticum* bud (clove), *Citrus unshiu* peel (*citrus unshiu* peel), *Oenothera tetraptera* (evening primrose), *Camellia japonica* (camellia), Centella, *Juglans regia* var. *orientis*, *Angelica acutiloba* root (Japanese angelica root), *Calendula officinalis* (common marigold), *Prunus persica* kernel (peach kernel), *Citrus aurantium* peel (bitter orange peel), *Zea mays* seed (corn), *Houttuynia cordata*, *Lycopersicon esculentum* (tomato), *Daucus carota* (carrot), *Allium sativum* (garlic), wild rose, malt, *Ophiopogon japonicus* tuber (ophiopogon tuber), *Petroselinum crispum* (common parsley), *Secale cereale* (rye), *Coix ma-yuen*, *Mentha arvensis* leaves (mentha herb), *Carica papaya* (papaya), *Hamamelis virginiane* leaves (witch-hazel leaves), Rosa (rose), *Chamaecyparis obtuse* (hinoki cypress), fucus, *Helianthus annuus*

(sunflower), *Eriobotrya japonica* (Japanese loquat), *Tussilago farfara* (coltsfoot), butcher's-broom, *Vitis* (grape), Placenta, *Corylus avellana* (European hazelnut), *Luffa aegyptiaca* (sponge gourd), *Carthamus tinctorius* (bastard saffron), *Tilia miqueliana, Paeonia suffruticosa* (tree peony), *Humulus lupulus* (common hop), *Macadamia tetraphylla* (macadamia nut), *Pinus koraiensis* (pine kernel), pinecone, *Aesculus hippocastanum, Melissa officinalis* (bee balm), *Melilotus officinalis* (melilot), *Prunus persica* (peach), barley malt, *Centaurea cyanus* (cornflower), Palmae (coconut family), *Eucalyptus globules* (eucalyptus), *Saxifraga stolonifera* (strawberry begonia), *Citrus junos* (Yuzu), Lilium (lily), *Coix lachrymal-jobi* seed (coix seed), *Artemisia princeps, Secale cereole* (common rye), *Arachis hypogaea* (peanut), *Lavandula vera* (lavender), *Malus domestica* (common apple), *Litchi chinensis* (lichi), lettuce, *Citrus limon* (lemon), *Astragalus sinicus* (milk vetch), *Rosmarinus officinalis* (rosemary), Lot, *Anthemis nobilis* (chamomile), *Sanguisorba officinalis* (great burnet), young plant of *Artemisia capillaris, Agrimonia pilosa* (agrimony), *Catalpa ovata* fruit (catalpa fruit), *Thujopsis dolabrata* (hiba arborvitae), *Euphorbia lathyris* seed (caper-spurge), *Plectranthus japonicus,* immature *Citrus aurantium* (immature orange), Senkishi, *Stellaria media* (chickweed), duckweed, *Artemisia capillaries, Ginkgo biloba* (maidenhair tree), *Platycodon grandiflorus* (balloon flower), Chrysanthemum, *Sasa veitchii* (kuma bamboo grass), *Sapindus mukorossi* (Chinese soapberry), and *Forsythia suspensa.*

Amino acids or salts thereof: These compounds include for example, ornithine, tryptophan, lysine, arginine, histidine, canavanine, glutamic acid, aspartic acid, serine, alanine, glycine, leucine, isoleucine, proline, threonine, valine, methionine, cystine, cysteine, hydroxyproline, phenylalanine, tyrosine, hydroxylysine, trimethylglycine, sodium aspartate, potassium aspartate, magnesium aspartate, calcium aspartate, sodium glutamate, potassium glutamate, magnesium glutamate, calcium glutamate, glutamic acid hydrochloride, cysteine hydrochloride, histidine hydrochloride, histidine acetate, histidine phosphate, lysine hydrochloride, lysine acetate, ornithine hydrochloride, ornithine acetate, tryptophan hydrochloride, glutamate arginine glutamate ornithine, glutamate lysine, aspartate lysine, aspartate ornithide and ε-aminocaproic acid.

Peptides: They include, for example, tripeptide (Arg-Gly-Asp), tetrapeptide (Arg-Gly-Asp-Ser) (JP-A-02-178207), a peptide represented by the formula (Arg-Pro-Phe-Phe)$_n$ (wherein n is an integer of 1-8) (JP-A-62-99315) and albumin.

Organic acids: They include, for example, citric acid, lactic acid, succinic acid, tartaric acid and kojic acid.

Vitamins and derivatives thereof: This group include, for example, vitamin $B_1$, $B_2$, $B_6$, $B_{12}$ and C, nicotinic acid, folic acid, pantothenic acid, p-aminobenzoic acid and biotin.

Inorganic acids: They include, for example, magnesium sulfate, potassium sulfate, sodium sulfate, magnesium chloride and sodium chloride.

Among these active ingredients, compounds soluble in an aqueous medium are particularly preferable. A term "soluble in an aqueous medium" means a component having solubilities in water and in oil as defined hereinbelow. Namely, it is an active ingredient having a solubility in water of 1% by weight or more, which is almost sufficient amount to exhibit an effect as an active ingredient, and also having a solubility in an representative oil, squalane, of 1% by weight or less.

Further, a water-soluble dyestuff should be a dyestuff which is soluble in water and does not color or stain the oil-absorbing powder of component (A). Such a dyestuff should have a solubility in water of 0.01% by weight or more, which is almost sufficient solubility for coloring, and a solubility in a representative oil, squalane, of less than 0.01% by weight. Namely, when 0.01% by weight of a dyestuff is added in squalane, the dyestuff preferably generates precipitation or separation of the dyestuff without coloring the solution homogeneously.

Such a water-soluble dyestuff includes, for example, water-soluble colors which are legally permitted to be admixed to a cosmetic such as: Blue No. 1 (C.I. 42090), Blue No. 2 (C.I. 73015), Blue No. 202 (C.I. 42052), Blue No. 203 (C.I. 42052), Blue No. 205 (C.I. 42090), Red No. 2 (C.I. 16185), Red No. 3 (C.I. 45430), Red No. 102 (C.I. 16255), Red No. 104 (C.I. 45410), Red No. 105 (C.I. 45440), Red No. 106 (C.I. 45100), Red No. 201 (C.I. 15850), Red No. 213 (C.I. 45170), Red No. 214 (C.I. 45170), Red No. 227 (C.I. 17200), Red No. 228 (C.I. 12085), Red No. 230 (C.I. 45380), Red No. 231 (C.I. 45410), Red No. 232 (C.I. 45440), Red No. 401 (C.I. 45190), Red No. 502 (C.I. 16155), Red No. 504 (C.I. 14700), Red No. 506 (C.I. 15620), Yellow No. 4 (C.I. 19140), Yellow No. 5 (C.I. 15985), Yellow No. 202 (C.I. 45350), Yellow No. 203 (C.I. 47005), Yellow No. 402 (C.I. 18950), Yellow No. 403 (C.I. 10316), Yellow No. 406 (C.I. 13065), Yellow No. 407 (C.I. 18820), Green No. 3 (C.I. 42053), Green No. 201 (C.I. 61570), Green No. 204 (C.I. 59040), Green No. 205 (C.I. 42095), Green No. 401 (C.I. 10020), Green No. 402 (C.I. 42085), Orange No. 205 (C.I. 15510), Orange No. 207 (C.I. 45425), Orange No. 402 (C.I. 14600), Brown No. 201 (C.I. 20170), Purple No. 401 (C.I. 60730), and Black No. 401 (C.I. 20470); water-soluble natural colors such as: flavin dyestuffs (riboflavin, etc.), quinone dyestuffs [laccaic acid, carminic acid (cochineal), kermesic acid, etc.], betacyanin dyestuff (betanin and the like), and flavonoids (safrol yellow, shisonin, rutin, and the like).

A mixture of two or more of component (B) can be used, and an active ingredient and a water-soluble dyestuff may also be used in combination. Further, component (B) is contained preferably in an amount of 0.000001-20% by weight of the whole composition. When component (B) is used together with an active ingredient, the active ingredient is contained preferably in an amount of 0.001-20% by weight, more preferably 0.01-10% by weight of the whole composition, from the viewpoint of maintaining an effective amount of the active ingredient. In addition, when a water-soluble dyestuff is used, the dyestuff is contained preferably in an amount of 0.000001-1% by weight, more preferably 0.0001-0.1% by weight of the whole composition, from the viewpoint of easy confirmation of the removal of the sebum from the skin by a color change due to absorption of the sebum.

The cosmetic of the present invention is produced by mixing components (A) and (B) and optional components. Component (B) is contained in the cosmetic in a state homogeneously dispersed and maintained among the particles or in the porous structure of component (A).

The cosmetic of the present invention may be made into a form that can be applied or adhered onto the skin for the purpose of absorbing the sebum. For example, a cosmetic can be made into the form of paste, cream, aerosol, lotion, milky lotion, essence or face pack, and a pack cosmetic(face pack) is preferable in view of effectiveness.

A pack cosmetic is used by applying or adhering onto the skin such as face. Dosage form thereof includes, for example, a wash off-type pack cosmetic wherein the cosmetic is applied to absorb the sebum and then washed off; a peel off-type pack cosmetic wherein after applying, the cosmetic is dried to absorb the sebum, then peeled off; and a sheet-type pack cosmetic wherein the cosmetic removes the sebum as well as horny plug and smudge of the skin or absorbs the sebum, and then is peeled off. The sheet-type pack cosmetic is particularly preferable in view of effectiveness.

In the case of preparing the cosmetic of the present invention in the form of a pack cosmetic, it is preferable that the pack cosmetic further contains, as component (C), a hydrous gel consisting of a water-soluble polymer and a cross-linking agent. The water-soluble polymers herein include polyacrylic acid, polymethacrylic acid, alginate, starch, agar, gelatin, pectin, casein, polyvinyl alcohol, poly(vinyl pyrrolidone) and polyethylene oxide.

A mixture of two or more of the water-soluble polymers may be used, and is contained preferably in an amount of 1-30% by weight, more preferably 2-15% by weight of the whole composition.

A cross-linking agent is a compound which causes a cross-linking reaction with the above-mentioned water-soluble polymer. The cross-linking agents include polyvalent metal salts such as water-soluble salts, for example, calcium chloride, aluminum chloride, potassium alum and aluminum sulfate; and salts slightly soluble in water or hardly soluble in water, for example, calcium hydroxide, aluminum hydroxide, calcium carbonate, calcium phosphate, aluminum stearate and calcium citrate.

The cross-linking agent is preferably added in an amount of 0.01-5 equivalents, more preferably 0.1-2 equivalents to the cross-linkable sites of the water-soluble polymer.

Further, among the pack cosmetics, a sheet-type pack cosmetic can be produced, for example, by mixing the above-mentioned components, impregnating a substrate fabric with the resulting composition or applying the composition onto the substrate fabric to form a sheet, and, if necessary, further applying facing with a polyethylene film. Alternatively, a sheet-type pack cosmetic can be obtained by spreading the composition on a facing film, covering the resulting film with a substrate fabric, and cutting the resulting sheet into pieces with a predetermined size.

The substrate fabric includes knitted or woven fabrics such as flannel and spun rayon; nonwoven fabrics such as felt and spun lace; papers; and plastic sheets.

The thickness of the substrate fabric is preferably 0.1-2.0 mm, more preferably 0.1-1.0 mm, and the thickness of the coating of the composition is preferably 0.1-2.0 mm, more preferably 0.1-1.0 mm. The total thickness is preferably 0.1-4.0 mm, more preferably 0.1-2.0 mm.

The shape and size of the sheet are not particularly limited, and a patch covering the whole face or a patch partially covering the face can be used.

In the case of preparing a peel off-type pack cosmetic as the cosmetic of the present invention, it is preferable to additionally use component (D) consisting of a film-forming water-soluble polymer.

The film-forming water-soluble polymers include synthetic polymers such as poly(vinyl alcohol), poly(vinyl pyrrolidone), poly(vinyl acetate), poly(meth)acrylate, polystyrene, polyalkylene oxide and silicone; and natural polymers such as cellulose, starch and proteins.

A mixture of two or more of the film-forming water-soluble polymer may be used and is contained preferably in an amount of 0.01-70% by weight, more preferably 5-40% by weight of the whole composition.

The peel off-type pack cosmetic can be produced, for example, by stirring and mixing components (A), (B) and (D) and other optional components according to a conventional method.

The cosmetic of the present invention may optionally contain, in addition to the above components, for example, solid or semisolid oils, liquid oils, hydrocarbons, higher alcohols, higher fatty acids, esters, silicones, lower alcohols, polyhydric alcohols, polysaccharides, synthetic polymer emulsions, surface active agents, thickeners, pH regulating agents, antioxidants, coloring agents, perfumes, antiseptics and water.

The cosmetic of the present invention is used by applying or adhering onto the face, leaving for about 15 minutes to 10 hours, and peeling off or washing off. For example, the sheet-type pack cosmetic can be applied before going to bed and peeled off after waking-up.

In the present invention, when an active ingredient is used as component (B) and the sebum is absorbed by the oil-absorbing powder in the applied cosmetic, said active ingredient is released in exchange for the absorbed sebum, whereby said active ingredient is effectively provided to the skin, and, as a result, the effect is maintained at a lower concentration compared with conventional cosmetics which contain a high concentration of the active ingredient. And said effect, as well as the effect of improving oiliness of the skin and worsening in makeup, can be recognized as the effects of the active ingredient such as moist- retaining feeling and moistness feeling when a component having a moisturizing effect is used. When a water-soluble dyestuff is used as component (B), said water-soluble dyestuff is released by absorption of the sebum to change the color of the part (for example, the color disappears and gradually changes to white), and a degree of the absorption of the sebum or removal of the sebum can be recognized and realized by the change of color.

EXAMPLE

Reference Example 1

For each of the oil-absorbing powders shown in Table 1, the amount of the absorbed squalane was measured by a method according to the above-described JIS K 5101. In addition, an average particle diameter of each powder was also measured using a laser diffraction/scattering type particle size distribution measuring equipment made by Horiba Ltd.

TABLE 1

| | Amount of absorbed squalane (mL/g) | Average Particle Diameter (μm) |
|---|---|---|
| Porous Vinyl Polymer (The polymer in Synthesis Example 1 of JP-A-63-316715) | 3.35 | 6.7 |
| Silicone-treated Mica Powder | 0.60 | 18 |

Reference Example 2

Solubilityies of 1% by weight of components (1) to (5), and those of 0.01% by weight of components (6) and (7) were examined by visual observation of the dissolving states of the components mixed at 25° C. with water or squalane. The results are shown in Table 2. Criteria for judgment:

TABLE 2

| Component (B) | Water | Squalane |
|---|---|---|
| (1) Seeweeds Extract | o | x |
| (2) Hamamelis Extract | o | x |
| (3) Arthaea Extract | o | x |
| (4) Hiba Extract | o | x |

TABLE 2-continued

| Component (B) | Water | Squalane |
|---|---|---|
| (5) Dipotassium Glycyrrhizinate | ○ | x |
| (6) Blue No. 1 | ○ | x |
| (7) Purple No. 401 | ○ | x |

○: Completely dissolved
x: Separated or precipitated without dissolution

Example 1

Sheet-type Pack Cosmetic

| (Component) | (% by weight) |
|---|---|
| (1) Porous Vinyl Polymer (Synthesis Example 1 in JP-A-63-316715) | 25.25 |
| (2) Glycerol | 25.8 |
| (3) Sodium Polyacrylate | 5.5 |
| (4) Polyacrylic Acid | 0.5 |
| (5) Dry Aluminium Hydroxide Gel | 0.4 |
| (6) Seeweeds Extract | 1.1 |
| (7) Hamamelis Extract | 0.01 |
| (8) Arthaea Extract | 1.0 |
| (9) Hiba Extract | 0.5 |
| (10) Dipotassium Glycyrrhizinate | 0.2 |
| (11) Methylparaben | 0.1 |
| (12) Odorless Menthol | 0.05 |
| (13) Ethanol | 0.275 |
| (14) Purified Water | Balance |

(Preparation Method)

Components (3) to (5) were homogeneously dispersed into component (2) using a kneader, and the resultant mixture was added with components (6) to (11) and (14) followed by homogeneously kneading, then added with component (12) and (13) followed by homogeneously kneading, and further added with component (1) followed by homogeneously kneading, to obtain a cosmetic. This cosmetic was uniformly coated (thickness:0.5 mm) on a polyester film, then covered with a nonwoven fabric made of polyester to form a sheet.

Example 2

Pack Cosmetic (Peel-off Type)

| (Component) | (% by weight) |
|---|---|
| Porous Vinyl Polymer (Synthesis Example 1 in JP-A-63-316715) | 25.0 |
| Polyvinyl Alcohol | 12.0 |
| Castol Oil hardened with Polyoxyethylene (40EO) | 1.0 |
| 1-Isostearoyl-3-myristoyl-glycerol | 1.0 |
| Glycerol | 5.0 |
| Seeweeds Extract | 1.1 |
| Methylparaben | 0.1 |
| Ethanol | 7.0 |
| Purified Water | Balance |

(Preparation Method)

The components of the above-described composition were stirred and kneaded to produce a peel off-type pack cosmetic.

Example 3

Pack Cosmetic (Wash Off-type)

| (Component) | (% by weight) |
|---|---|
| Porous Vinyl Polymer (Synthesis Example 1 in JP-A-63-316715) | 25.0 |
| Acidic Hetero Polysaccharides | 0.1 |
| dl-α-Tocopherol Nicotinate | 1.0 |
| Castol Oil hardened with Polyoxyethylene (40EO) | 1.0 |
| 1-Isostearoyl-3-myristoyl-glycerol | 1.0 |
| Calboxylated Vinyl Polymer | 0.5 |
| Glycerol | 4.0 |
| L-Arginine | 0.5 |
| Methylparaben | 0.10 |
| Purified Water | Balance |

(Preparation Method)

The components of the above-described composition were stirred and kneaded to produce a pack cosmetic.

Example 4

Cream

| (Component) | (% by weight) |
|---|---|
| Porous Vinyl Polymer (Synthesis Example 1 in JP-A-63-316715) | 30.0 |
| Seeweeds Extract | 1.1 |
| Hamamelis Extract | 0.01 |
| Althaea Extract | 1.0 |
| Hiba Extract | 0.5 |
| Cross-linked Polyether-modified Silicone | 2.7 |
| Silicone Oil (10 cs) | 27.0 |
| Glycerol | 15.0 |
| Sodium Citrate | 1.50 |
| Methylparaben | 0.10 |
| Purified Water | Balance |

(Preparation Method)

The components of the above-described 5 composition were stirred and kneaded to produce a cream.

Example 5

Milky Lotion

| (Component) | (% by weight) |
|---|---|
| Porous Vinyl Polymer (Synthesis Example 1 in JP-A-63-316715) | 15.0 |
| Seeweeds Extract | 1.1 |
| Hamamelis Extract | 0.01 |
| Althaea Extract | 1.0 |
| Hiba Extract | 0.5 |
| Silicone Oil (6 cs) | 2.0 |
| Glycerol | 15.0 |
| Polyoxyethylenesorbitan Monostearate | 15.0 |
| Sorbitan Monostearate | 1.5 |

-continued

| (Component) | (% by weight) |
|---|---|
| Cetyl Alcohol | 1.2 |
| Stearyl Alcohol | 0.8 |
| Carboxylated Vinyl Polymer | 0.2 |
| Potassium Hydroxide | 0.05 |
| Methylparaben | 0.03 |
| Purified Water | Balance |

(Preparation Method)

The components of the above-described composition were stirred and kneaded to produce a milky lotion.

Comparative Example 1

The same procedure as in Example 1 was repeated except that the components of seaweeds extract, hamamelis extract, althaea extract, hiba extract and potassium glycyrrhizinate were omitted, to produce a sheet-type pack cosmetic.

Comparative Example 2

The same procedure as in Example 1 was repeated except that a silicone-treated mica powder was used instead of the porous vinyl polymer, to produce a sheet-type pack cosmetic.

Comparative Example 3

The same procedure as in Example 2 was repeated except that the seaweeds extract was omitted, to produce a peel off-type pack cosmetic.

Comparative Example 4

The same procedure as in Example 3 was repeated except that L-arginine was omitted and 0.125% by weight of potassium hydroxide was added, to produce a wash off-type pack cosmetic.

Comparative Example 5

The same procedure as in Example 4 was repeated except that the components of seaweeds extract, hamamelis extract, althaea extract and hiba extract were omitted, to produce a cream.

Comparative Example 6

The same procedure as in Example 5 was repeated except that the components of seaweeds extract, hamamelis extract, althaea extract and hiba extract were omitted, to produce an milky lotion.

Test Example 1

Effects of improving oiliness, preventing worsening in makeup and moistness feeling were evaluated when the cosmetics obtained in Examples 1 to 5 and Comparative Examples 1 to 6 were used. The results are shown in Table 3.

(Evaluation Method)
(1) Effects of improving oiliness and preventing worsening in makeup:

The sheet-typ pack cosmetics obtained in Example 1, Comparative Example 1 and Comparative Example 2 were applied onto the faces of 10 female panelists, and peeled off after 6 hours. The peel off-type pack cosmetics obtained in Example 2 and Comparative Example 3 were applied to their faces, and peeled off after drying for 30 minutes. The wash off-type pack cosmetics obtained in Example 3 and Comparative Example 4 were applied onto their faces, and washed off after being left for 30 minutes. Each of the creams and milky lotions obtained in Examples 4 and 5 and Comparative Examples 5 and 6 was applied onto their faces, and left for 30 minutes. Effects of improving oiliness and preventing worsening in makeup brought about by these cosmetics after use were organoleptically evaluated, and ranked according to the following criteria.

○: Not less than 7 panelists evaluated to be "effective".
Δ: From 4 to 6 panelists evaluated to be "effective".
X: Not more than 3 panelists evaluated to be "effective".

(2) Moistness feeling

Similarly as in (1), effects of each cosmetic after use were evaluated by 10 female panelists and ranked according to the following criteria.

TABLE 3

| | Example | | | | | Comparative Example | | | | | |
|---|---|---|---|---|---|---|---|---|---|---|---|
| | 1 | 2 | 3 | 4 | 5 | 1 | 2 | 3 | 4 | 5 | 6 |
| Improvement on Oiliness | ○ | ○ | ○ | ○ | ○ | ○ | x | Δ | Δ | Δ | Δ |
| Prevention of Worsening in Makeup | ○ | ○ | ○ | ○ | ○ | ○ | x | Δ | Δ | Δ | Δ |
| Moistness Feeling | ○ | ○ | ○ | ○ | ○ | x | Δ | x | x | x | x |

○: Not less than 7 panelists evaluated to be "effective".
Δ: From 4 to 6 panelists evaluated to be "effective".
x: Not more than 3 panelists evaluated to be "effective".

All of the cosmetics of the present invention were excellent in improvement on oiliness, prevention of worsening in makeup and moistness feeling.

Example 6

Sheet-type Pack Cosmetic

| (Component) | (% by weight) |
|---|---|
| (1) Porous Vinyl Polymer (Synthesis Example 1 in JP-A-63-316715) | 25.25 |
| (2) Blue No. 1 | 0.005 |
| (3) Glycerol | 25.80 |
| (4) Sodium Polyacrylate | 5.50 |
| (5) Polyacrylic Acid | 0.50 |
| (6) Dry Aluminium Hydroxide Gel | 0.40 |
| (7) Methylparaben | 0.10 |
| (8) Odorless Menthol | 0.05 |
| (9) Ethanol | 0.275 |
| (10) Purified Water | Balance |

(Preparation Method)

Components (4), (5) and (6) were homogeneously dispersed into component (3) using a kneader, and the resultant mixture was added with components (2), (7) and (10) followed by homogeneously kneading. Subsequently, the mixture was added with component (8) and (9) followed by homogeneously kneading, and further added with component (1) followed by homogeneously kneading, to obtain a cosmetic. This cosmetic was uniformly applied (thickness:0.5 mm) onto a polyester film, and then covered with a nonwoven fabric made of polyester to form a sheet.

Example 7

The same procedure as in Example 6 was repeated except that purple No.401 was used instead of blue No.1, to produce a sheet type pack cosmetic.

Example 8

Pack Cosmetic (Peel Off-type)

| (Component) | (% by weight) |
|---|---|
| Porous Vinyl Polymer (Synthesis Example 1 in JP-A-63-316715) | 25.0 |
| Blue No. 1 | 0.005 |
| Polyvinyl Alcohol | 12.0 |
| Castol Oil hardened with Polyoxyethylene (40EO) | 1.0 |
| 1-Isostearoyl-3-myristoyl-glycerol | 1.0 |
| Glycerol | 5.0 |
| Methylparaben | 0.10 |
| Ethanol | 7.00 |
| Purified Water | Balance |

(Preparation Method)

The components of the above-described composition were stirred and kneaded to produce a peel off-type pack cosmetic.

Comparative Example 7

The same procedure as in Example 6 was repeated except that blue No.1 was omitted, to produce a peel off-type pack cosmetic.

Comparative Example 8

The same procedure as in Example 6 was repeated except that a silicone-treated mica powder was used instead of the porous vinyl polymer, to produce a sheet-type pack cosmetic.

Comparative Example 9

The same procedure as in Example 8 was repeated except that blue No.1 was omitted, to produce a peel off-type pack cosmetic.

Test Example 2

The cosmetics obtained in Examples 6 to 8 and Comparative Examples 7 to 9 were evaluated with regard to improvement on oiliness, prevention of worsening in makeup, as well as color change and effectiveness feeling. The results are shown in Table 4.

(Evaluation Method)
(1) Improvement on oiliness and prevention of worsening in makeup:
Evaluation was effected similarly as in Test Example 1.
(2) Color changes of pack cosmetics:
Each of the pack cosmetics was examined by a visual examination after applying and peeling off, and ranked as "○" if a color of the sheet on an applied face was changed with a partial disappearance of a color, and as "X" if the color was not changed.

(3) Effectiveness feeling
Similarly as in (1), each of the pack cosmetics was observed by 10 female panelists after applying and peeling off from their faces, and an extent of actual feeling of sebum-removal was judged according to the following criteria.

TABLE 4

| | Example | | | Comparative Example | | |
|---|---|---|---|---|---|---|
| | 6 | 7 | 8 | 7 | 8 | 9 |
| Improvement on Oiliness | ○ | ○ | ○ | ○ | x | ○ |
| Prevention of Worsening in Makeup | ○ | ○ | ○ | ○ | x | Δ |
| Color change of Pack Cosmetic (Disappearance) | ○ | ○ | ○ | x | x | x |
| Effectiveness Feeling | ○ | ○ | ○ | x | x | x |

○: Not less than 7 panelists evaluate to be "actually felt as effective".
Δ: From 4 to 6 panelists evaluated to be "actually felt as effective".
x: Not more than 3 panelists evaluated to be "actually felt as effective.

All of the pack cosmetics obtained in Examples 6 to 8 were excellent in improvement on oiliness and prevention of worsening in makeup, showed clear changes in the color of cosmetics, and had good actual feelings of effectiveness.

INDUSTRIAL APPLICABILITY

The cosmetic of the present invention can adequately absorb sebum and thus exhibits an excellent effect of improving or preventing oiliness of the skin and worsening in makeup. By selecting the compound which is released from the cosmetic in exchange for the absorbed sebum, the substance having an ability to improve the skin qualities such as moistness, tightness and tension can effectively penetrate into the skin, and a bodily feeling of the removal of the sebum can be imparted to users thereby.

What is claimed is:
1. A cosmetic comprising the following components (A) and (B):
   (A) an oil-absorbing powder having a squalane-absorbing ability of 1 ml/g or more; and
   (B) a compound having an affinity for component (A) which is lower than an affinity of sebum for component (A);
   wherein:
   the cosmetic has an ability to absorb the sebum and release component (B) in exchange for the sebum when the cosmetic is applied to the skin;
   component (B) is present in the cosmetic in a homogeneously dispersed state among or in a porous structure of particles of component (A);
   component (B) comprises one or more compounds selected from the group consisting of an active ingredient which is soluble in an aqueous medium and a water-soluble dyestuff; and
   the active ingredient comprises one or more substances selected from the group consisting of extracts of animals or plants, amino acids or salts thereof, peptides, proteins, organic acids, vitamins and vitamin derivatives, urea and inorganic salts,
   wherein the vitamins and vitamin derivatives are at least one selected from the group consisting of vitamins B1, B2, B6, B12, E, and C, nicotinic acid, folic acid, pantothenic acid, p-aminobenzoic acid, biotin, and dl-α-Tocopherol nicotinate.

2. The cosmetic according to claim 1, wherein component (A) comprises a porous powder having an average particle size of 0.005-30 μm.

3. The cosmetic according to claim 1, wherein component (A) comprises a hydrophobic oil-absorbing powder.

4. The cosmetic according to claim 1, wherein component (A) comprises a vinyl polymer obtained by polymerizing one or more monomers selected from the group consisting of vinyl acetate, N-vinyl pyrrolidone, methacrylates, acrylates, styrene and divinylbenzene.

5. The cosmetic according to claim 1, wherein component (A) comprises a porous hydrophobic polymer.

6. The cosmetic according to claim 1, wherein component (B) comprises one or more compounds selected from the group consisting of humectants, pharmacologically active substances, antibiotics and anti-inflammatory agents.

7. The cosmetic according claim 1, wherein the active ingredient has a solubility in water of 1% by weight or more and a solubility in squalane of 1% by weight or less.

8. The cosmetic according to claim 1, wherein:
component (B) comprises the water-soluble dyestuff; and
the water-soluble dyestuff has a solubility in water of 0.01% by weight or more and a solubility in squalane of less than 0.01% by weight.

9. The cosmetic according to claim 1, wherein:
component (A) is present in an amount 10-60% by weight relative to a total weight of the cosmetic; and
component (B) is present in an amount of 0.000001-20% by weight relative to the total weight of the cosmetic.

* * * * *